United States Patent
Lantzsch

Patent Number: 6,114,581
Date of Patent: Sep. 5, 2000

[54] METHOD FOR PRODUCING N-ALKYL-N'-NITROGUANIDINES

[75] Inventor: Reinhard Lantzsch, Wuppertal, Germany

[73] Assignee: Bayer Aktiengesellschaft, Leverkusen, Germany

[21] Appl. No.: 09/381,675

[22] PCT Filed: Mar. 12, 1998

[86] PCT No.: PCT/EP98/01428

§ 371 Date: Sep. 22, 1999

§ 102(e) Date: Sep. 22, 1999

[87] PCT Pub. No.: WO98/43951

PCT Pub. Date: Oct. 8, 1998

[30] Foreign Application Priority Data

Mar. 27, 1997 [DE] Germany .................. 197 12 885

[51] Int. Cl.[7] .................. C07C 277/02; C07C 277/08
[52] U.S. Cl. .................................................. 564/108
[58] Field of Search ............................................ 564/108

[56] References Cited

FOREIGN PATENT DOCUMENTS

| 376279 | 5/1993 | European Pat. Off. . |
| 428941 | 5/1995 | European Pat. Off. . |

OTHER PUBLICATIONS

Can. J. Chem., vol. 36, (month unavailable) 1958, pp. 737–743, Alkylguanidine Nitrates and Alkylnitroguanidines, Paul E. Gagnon, Jean L. Boivin, Paul A. Boivin, and John H. Dickson.

Zeitschrift für Angewante Chemie, 42 (month unavailable) 1929, p. 379, Über ein Verfahren zur bequemen Darstellung luftbeständiger Salze des Methylguanidins, Von Wilhelm Traube und Kurt Gorniak.

JACS, 55, Feb. 1933, p. 739, Alkyl–Nitroguanidines.

Chem. Abstracts, vol. 52, p. Nos. 18212 & 18213, (month unavailable) 1958.

JACS, Sep. 1927, vol. 49, p. 2303, Alkyl–Nitroguanidines, By Tenney L. Davis and Stewart B. Luce.

JACS, vol. 69, p. 3028, (month unavailable) 1947, Preparation and Properties of N–Methyl–N–Nitroso–N'–Nitroguanidine, by A. F. McKay and George F. Wright.

JAC, vol. 76, p. 1877, Apr. 5, 1954, The Preparation and Reactions of 2–Alkyl–1 (OR 3)–Nitro–2–Thiopseudourea. Part I. Reaction with Amines[1] By Lawrence Fishbein and John A. Gallaghan.

JACS, 55, p. 731, Feb., 1933, Alkyl–Nitroguanidines. Dearrangement and Preparation by Nitration By Tenney L. Davis and Robert C. Elderfield.

*Primary Examiner*—Peter O'Sullivan
*Attorney, Agent, or Firm*—Joseph C. Gil

[57] ABSTRACT

The invention relates to a novel process for the preparation of N-alkyl-N'-nitroguanidines of the formula (I)

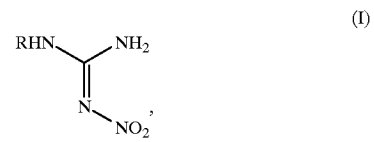

in which

R is $C_1$–$C_6$-alkyl, by neutralizing alkylamine with nitric acid, then reacting it with cyanamide, and dehydrating the alkylguanidine nitrate formed.

4 Claims, No Drawings

METHOD FOR PRODUCING N-ALKYL-N'-NITROGUANIDINES

This application is a 371 of PCT/EP98/01428 filed Mar. 12, 1998.

The invention relates to a novel process for the preparation of N-alkyl-N'-nitroguanidines.

It is known that N-alkyl-N'-nitroguanidines are obtained by firstly nitrating 5-methylisothiuronium sulphate of the formula (A) in a customary manner and then, in a second reaction stage, substituting the methylmercapto group for alkylamine in accordance with the following equation:

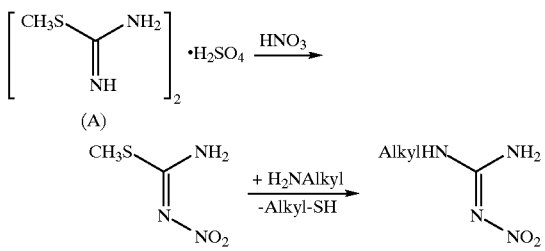

(cf. to this JACS 76, 1877 (1954)).

This process does, however, have the disadvantage that it is a two-stage reaction. Although the yields in both stages are relatively good, cleavage of the alkylmercaptan, in particular of methylmercaptan, particularly when carried out on an industrial scale, presents technical problems.

It is also known that N-alkyl-, in particular N-methyl-N'-nitroguanidines can be obtained by reacting an alkaline solution (potassium hydroxide) of nitroguanidine with alkyl (in particular methyl)amine hydrochloride at 60° C. in accordance with the following equation:

for example

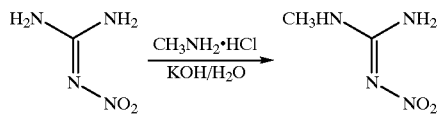

(cf. to this JACS 69, 3028 (1947) and 49, 2303 (1927)).

In this process, the yields and, in particular, the purity of the end products, which have to be purified in complex procedures, are very unsatisfactory. Relatively large amounts of alkyl(methyl)urea form as by-products with the development of gaseous $N_2O$. Added to this are large amounts of wastewater and the fact that nitroguanidine is a relatively expensive starting material.

It is further known that N-alkyl-N'-nitroguanidines can be obtained by nitration of alkylguanidine sulphates (cf. to this JACS, 55, 731 (1933)).

This process variant too has the disadvantage of an unsatisfactory yield and a relatively large amount of wastewater.

A further known preparation method is the dehydration of alkylguanidine nitrates using sulphuric acid (cf. to this JACS, 55, 739 (1933)).

Although this process proceeds in relatively good yields, the availability of the starting materials, such as, for example, of methylguanidine nitrate, is very poor (cf. to this Zeitschrift fir angewandte Chemie 42, 380 (1929)).

For the preparation of the nitrate, barium nitrate must be used, and the yield is only 40to50%.

The reaction of amine nitrates with calcium cyanamide or dicyandiamide is also unsatisfactory (Can. J. Chem. 36, 737–743 (1958)), since the amine must be used in a 4-fold excess.

It has now been found that N-alkyl-N'-nitroguanidines of the formula (I)

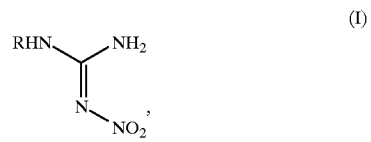

in which
R is $C_1$–$C_4$-alkyl,
are obtained when alkylamine, optionally in aqueous solution and optionally in the presence of an organic solvent, is neutralized with nitric acid, then concentrated by evaporation and reacted with cyanamide in the presence of an organic solvent and optionally under pressure at temperatures between 80° C. and 180° C., and the alkylguanidine nitrate formed is dehydrated.

Surprisingly, the novel process can be used to obtain N-alkyl-N'-nitroguanidines of in the formula (I) in a simple manner in very good yields and in high purity, although from the prior art it was to be expected that the use of equimolar amounts of amine (or only a very slight excess) would produce only low yields.

The novel reaction thus has the advantage that it can be carried out without or with only a small amount of excess amine nitrate, thus making it more cost-effective and less of a burden on the environment.

The compounds which can be prepared by the novel process are generally defined by the formula (I). In this formula, R is preferably alkyl having from 1 to 4 carbon atoms, such as, in particular, methyl and ethyl.

If, for example, methylamine is used as starting material, the course of the reaction for the novel process can be outlined by the following equation:

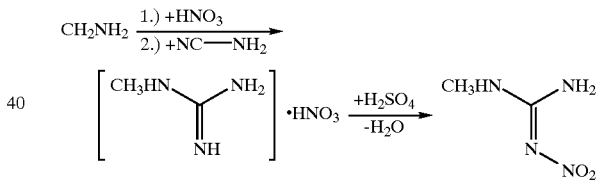

The starting materials alkylamine and cyanamide are generally known compounds in organic chemistry.

Suitable organic solvents are all organic diluents which are inert towards the reactants. These include, preferably, alcohols, such as methanol, ethanol or butanol, and ethers, such as ethylene glycol dimethyl ether, ethylene glycol diethyl ether, diethylene glycol dimethyl ether or methyl tert-amyl ether.

The reaction with cyanamide is preferably carried out with the exclusion of oxygen in a sealed vessel so that a pressure slightly above atmospheric up to 20 bar, preferably up to 6 bar, can form.

During the reaction with cyanamide, the reaction temperatures can be varied within a relatively wide range. The reaction is generally carried out at temperatures between 80° C. and 180° C., preferably between 100° C. and 150° C.

Suitable dehydrating agents are, in principle, all water-eliminating agents. Preferred examples which may be mentioned are sulphonic acids, sulphuric acid and trifluoroacetic acid.

The novel process is preferably carried out using equimolar amounts. It is, however, also possible to use an excess of alkylamine or a slight excess of cyanamide.

Work-up can be carried out in the usual manner.

The N-alkyl-N'-nitroguanidines of the formula (I), which are to be prepared by the novel process, such as, in particular, N-methyl-N'-nitroguanidine, can be used as intermediates for the preparation of biologically active compounds, for example of insecticides (cf. e.g. EP-A 0 376 279 and EP-A 0 428 941).

PREPARATION EXAMPLES

EXAMPLE 1

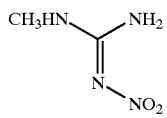

5.2 g (0.05 mol) of a 30% strength aqueous methylamine solution are neutralized using about 4.2 g of 75% strength nitric acid, and then the water is distilled off under reduced pressure.

15 ml of n-butanol and 2.2 g of cyanamide are added, and the mixture is introduced into a 50 ml autoclave. The mixture is then heated for 8 hours at an internal temperature of 130° C. After decompression, butanol is distilled off, and 8.5 ml of concentrated sulphuric acid are carefully added to the residue with cooling and stirring at from −5° C. to +5° C. After 30 minutes, 50 g of ice are added, and the mixture is filtered and then washed with a small amount of cold water.

This gives 5.5 g (93% of theory) of N-methyl-N'-nitroguanidine having a melting point of 160° C.

EXAMPLE 2

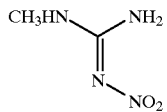

5.2 g (0.05 mol) of a 30% strength aqueous methylamine solution are neutralized using about 4.2 g of 75% strength nitric acid, and then the water is distilled off under reduced pressure.

15 ml of n-butanol and 2.2 g of cyanamide are added, and the mixture is introduced into a 50 ml autoclave. The mixture is then heated for 8 hours at an internal temperature of 140° C. After decompression, the mixture is cooled to from 0° C. to 5° C. and filtered. The filter cake is dried, and 9.5 ml of concentrated sulphuric acid are carefully added with cooling and stirring at from −5° C. to +5° C. After 20 minutes, 50 g of ice are added, and the mixture is filtered and then washed with a small amount of cold water.

This gives 5.3 g (89.6% of theory) of n-methyl-N'-nitroguanidine having a melting point of 160° C.

What is claimed is:

1. A process for the preparation of N-alkyl-N'-nitroguanidines of the formula (I)

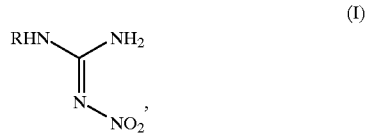

(I)

in which

R is $C_1$–$C_6$-alkyl, comprising neutralizing alkylamine with nitric acid, then reacting with cyanamide, and dehydrating the alkylguanidine nitrate formed.

2. The process of claim 1, wherein the reaction with cyanamide is carried out under pressure at temperatures between 80° C. and 180° C.

3. The process of claim 1, wherein

R is alkyl having from 1 to 4 carbon atoms.

4. The process of claim 1 wherein the reaction takes place in organic diluents which are inert towards the reactants.

* * * * *